United States Patent [19]
Coulter et al.

[11] 3,968,429
[45] July 6, 1976

[54] PARTICLE ANALYZER OF THE COULTER TYPE INCLUDING COINCIDENCE ERROR CORRECTION CIRCUITRY

[75] Inventors: Wallace H. Coulter, Miami Springs; Walter R. Hogg, Miami Lakes, both of Fla.

[73] Assignee: Coulter Electronics, Inc., Hialeah, Fla.

[22] Filed: July 9, 1975

[21] Appl. No.: 594,209

Related U.S. Application Data

[63] Continuation-in-part of Ser. No. 443,428, Feb. 19, 1974, Pat. No. 3,940,691.

[52] U.S. Cl...................... 324/71 CP; 235/92 PC; 328/41
[51] Int. Cl.².......................................... G01N 27/00
[58] Field of Search............. 324/71 CP; 235/92 PL; 328/41

[56] References Cited
UNITED STATES PATENTS

| | | | |
|---|---|---|---|
| 3,209,130 | 9/1965 | Schmidt | 235/92 PC |
| 3,649,820 | 3/1972 | Totsuka et al. | 235/92 PL |
| 3,705,295 | 12/1972 | Betz | 235/92 PL |
| 3,737,633 | 6/1973 | Collineau | 324/71 CP |
| 3,936,740 | 2/1976 | Hogg et al. | 324/71 CP |

*Primary Examiner*—R. V. Rolinec
*Assistant Examiner*—Vincent J. Sunderdick
*Attorney, Agent, or Firm*—Silverman & Cass, Ltd.

[57] ABSTRACT

A particle analyzer of the Coulter type has at least first and second sensing zone arrangements, each having substantially the same dimensions and each generating a train of particle pulses in response to passage through the respective sensing zone of a sample containing a plurality of particles to be counted. A summing circuit connected to the output of each sensing zone sums together each of the trains of particle pulses to develop a summed train of pulses. Additional circuitry is connected to each sensing zone and the summing circuitry. This circuitry is operative to change mathematically at least the number of particle pulses in the summed train of particle pulses. The mathematically changed summed train of pulses and the train of pulses from the first and second sensing zones then are accumulated to produce an error corrected particle pulse count.

16 Claims, 4 Drawing Figures

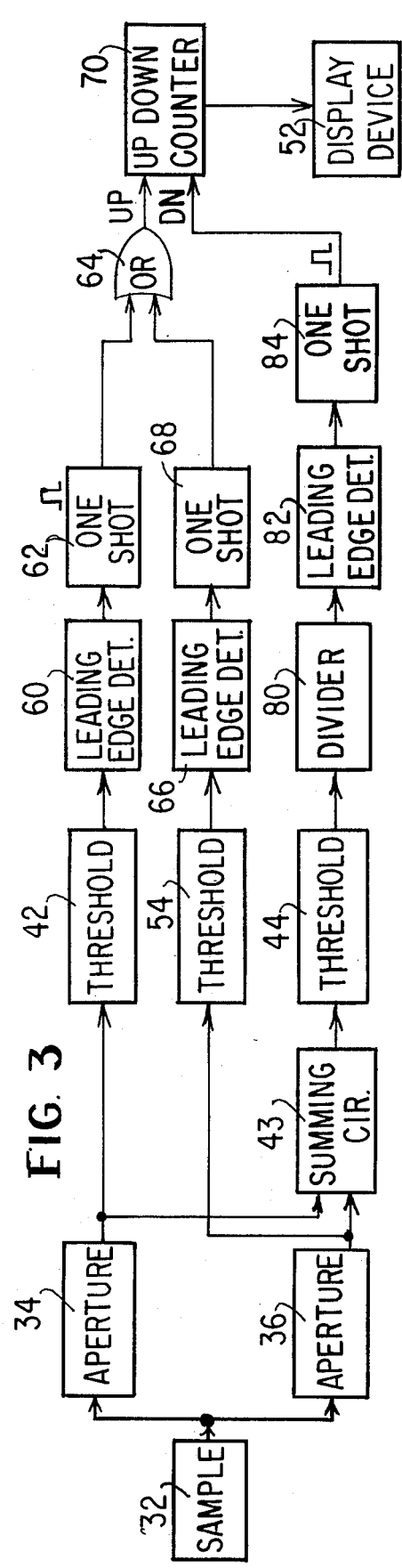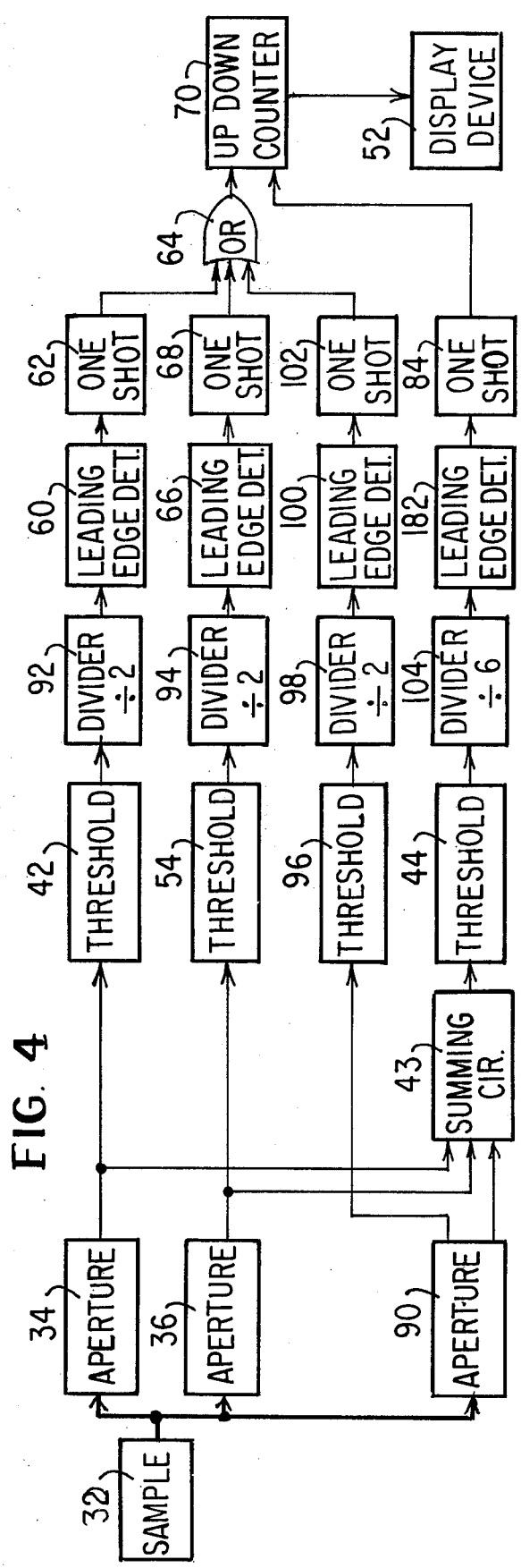

PARTICLE ANALYZER OF THE COULTER TYPE INCLUDING COINCIDENCE ERROR CORRECTION CIRCUITRY

CROSS-REFERENCE TO RELATED APPLICATIONS

This application is a continuation-in-part of U.S. patent application Ser. No. 443,428, now patent No. 3,940,691 February 19, 1974 and assigned to the same Assignee.

This application is related to U.S. patent application Ser. No. 454,793 filed Mar. 26, 1974 and entitled METHODS AND APPARATUSES FOR CORRECTING COINCIDENCE COUNT INACCURACIES IN A COULTER TYPE OF PARTICLE ANALYZER, which is assigned to the same Assignee and which is incorporated herein by this reference to the extent necessary.

BACKGROUND OF THE INVENTION

This invention is directed to particle counting apparatuses which provide a statistical correction to a detected train of particle derived count pulses, such that effective random coincidence inaccuracies of count do not induce ultimate counting error.

The particle counting apparatuses concerned employ particle sensing zones in which more than one particle might reside at any one time and thereby randomly generate a coincidence condition. This invention particularly is directed to, but not limited to the determination of nonelectrical properties, such as size and count of microscopic particles, by measuring electrical properties (Patent Office class 324-71NE).

Now well known in the art of electronic particle counting and analyzing is apparatus marketed primarily under the trademark "Coulter Counter." Such apparatus and portions thereof are disclosed in several United States Pats., for example Nos. 2,656,508; 2,985,830; and 3,259,842 (each in class 324-71). A significantly important portion of such Coulter type of apparatus is the minute scanning aperture or scanning ambit or sensing zone relative to or through which are to pass and be detected single particles at a rate often well in excess of one thousand per second. Because of the dimensions of the scanning aperture, and particle concentration, there frequently results the coincidence of two particles in the scanning ambit. As a result, there is effectively detected and counted only one particle, not two.

Although such primary form of coincidence loss of count is of a random nature, by reason of the large number of particles counted, it is predictable with considerable statistical accuracy. Several mathematical formulae approximate this loss very closely. A relatively simple one of such formulae is: $N' = K N^2$ in which $N'$ = the total number of coincidences, i.e., the required addend; $K$ = a constant which relates primarily to the dimensions of the scanning elements of the apparatus and $N$ = the detected number of particles, the augend. Accordingly, the true or corrected count $N_0$ will equal the sum of $N+N'$.

In the above noted parent application, Ser. No. 443,428 filed Feb. 19, 1974 methods and apparatus are disclosed for correcting coincidence count inaccuracies in a Coulter type of particle analyzer. In that patent application, it is stated that an error corrected particle pulse count can be obtained using another of these approximating formulae, namely, $$N_R = N_0 (1 - K N_0) \qquad (1)$$

wherein $N_0$ is the true or corrected count, $N_R$ is the raw count, and $K$ is a constant which relates primarily to the dimensions of the scanning elements of the apparatus. This latter approximation is equally valid, but results in much simpler computations. It should be pointed out that the equal sign here and in all other equations of this nature does not indicate exact equality, but merely statistically probably equality.

The copending application further states that two formulas such as formula (1) above, relating counts taken under different conditions, can be solved simultaneously yielding an equation for $N_0$ in terms of two related raw counts $N_1$ and $N_2$ only, thus eliminating K, a parameter which is difficult to ascertain. The equation for $N_0$, stated in terms of $N_1$ and $N_2$ only, is different for each way in which the two related counts $N_1$ and $N_2$ are developed. The two related counts are developed:

a. by passing a sample volume through different scanning apertures having a known difference in their critical volume relationship to obtain $N_1$ and $N_2$;

b. by passing a sample volume through different scanning apertures having the same critical volume and using one output as $N_1$ and the sum of the outputs as $N_2$;

c. by passing two different dilutions of known dilution relationship of the sample through a single scanning aperture to obtain $N_1$ and $N_2$;

d. by passing one sample through one scanning aperture to generate $N_1$ and, by use of delaying and adding $N_1$ to itself, to form $N_2$.

An equation for $N_0$ stated in terms of $N_1$ and $N_2$ only, is given in the copending application for each of these ways of developing $N_1$ and $N_2$.

The raw counts $N_1$ and $N_2$ developed using one of the above noted methods are mathematically manipulated then accumulated in accumulators in order to yield the true or corrected count.

SUMMARY OF THE INVENTION

In practicing this invention a particle analyzer of the Coulter type is provided for automatically developing an error corrected pulse count in response to particle pulses which are subject to coincidence error. The particle counter includes at least first and second sensing zone arrangements, each having substantially the same dimensions, and each generating a train of particle pulses in response to passage through the sensing zone of a sample containing a plurality of particles to be counted. Aliquots of the same sample each are scanned simultaneously by a sensing zone. A summing circuit coupled to each of the sensing zone arrangements sums together each of the trains of particle pulses to develop a summed train of pulses comprising all pulses from the sensing zones. Circuitry is coupled to the summing circuit and to each of the sensing zone arrangements. This circuitry receives each generated train of particle pulses from each of the sensing zone arrangements and the summed train of particle pulses and changes mathematically at least the number of particle pulses in the summed train of pulses in accordance with a particular mathemaical formula. Each train of particle pulses and mathematically changed summed train of pulses then is accumulated in an accumulation device in order to develop the error corrected particle pulse count.

BRIEF DESCRIPTION OF THE DRAWINGS

FIG. 3 is a more detailed block diagram of the particle analyzer of FIG. 3; and

FIG. 4 is a block diagram of another embodiment of this invention.

DETAILED DESCRIPTION OF THE PREFERRED EMBODIMENTS

In parent patent application Ser. No. 443,428 now U.S. Pat. No. 3,940,691 there is shown and described with respect to FIG. 4 therein an embodiment of a Coulter type particle detector which operates upon the premise that a single sample containing particles to be counted, passing through a single aperture can provide two particle counts $N_1$ and $N_2$ which are raw or uncorrected for coincidence errors. To accomplish such a goal, one of the raw counts, $N_2$, is created artificially from the same pulse train that generates the count $N_1$. The second pulse train and second pulse count $N_2$ is a synthesized double concentration count of $N_1$.

By substitution into equation (1) above;

(2) $N_1 = N_0 (1 - KN_0)$; and (3) $N_2 = 2N_0 (1 - 2KN_0)$; by multiplication equation (3) becomes;

(4) $N_2 = 2N_0 - 4KN_0^2$; multiplying equation (2) by four yields (5) $4N_1 = 4N_0 - 4KN_0^2$; subtracting equation (4) from equation (5) and solving for $N_0$ yields, (6) $N_0 = 2N_1 - (N_2/2)$ As noted in the Parent Application, equation (6) can be easily implemented in electronic circuitry which can continuously process the particle pulses from the pulse trains representing the raw counts $N_1$ and $N_2$ to provide a true or corrected count. For a detailed explanation of this circuitry reference is made to FIG. 4 and the description associated therewith in the parent application Ser. No. 443,428 now U.S. Pat. No. 3,940,691.

Although an artificially doubled concentration is described above and shown and described in the Parent Application, it is to be understood that structure shown therein is one, rather simple particular implementation. An alternate embodiment to the embodiment noted above is shown in FIG. 1 herein.

Figure 1:
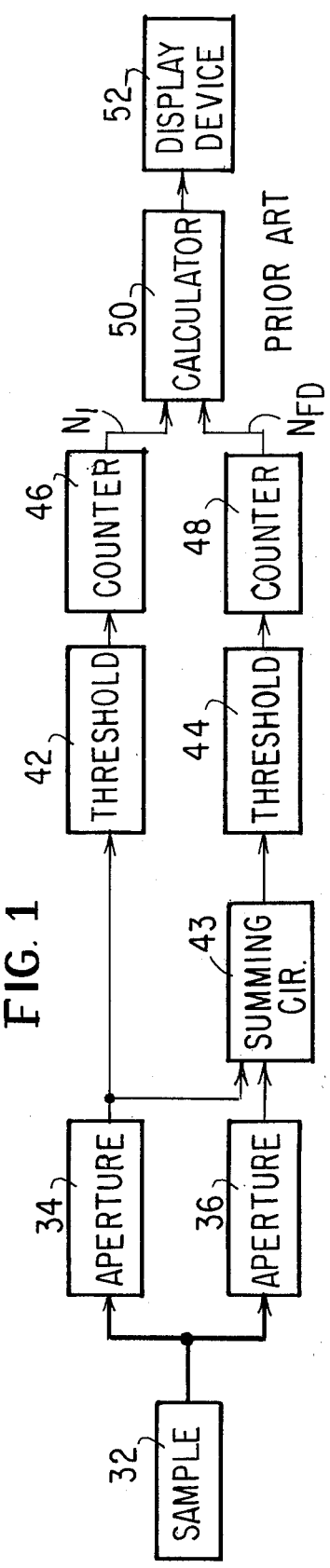
FIG. 1 is a block diagram of a prior art particle analyzer employing coincidence error correction circuitry.

Referring to FIG. 1, there is shown an arrangement in which a common source of particle sample 32 feeds into two aperture arrangements 34 and 36. Details of plural aperture setups are disclosed in U.S. Pat. Nos. 3,444,463, 3,444,464 and 3,549,994 (Class 324-71). It is to be assumed herein that the "aperture" blocks contain not only an aperture wafer and aperture but also aperture tubes, beakers, sample moving and measuring structures, circuitry and counter starting and stopping structures, electrodes, etc., all well known and disclosed in the patents cited herein.

If the particle analyzer is other than of the Coulter type, the blocks 34 and 36 will contain the appropriate sensing zone arrangements. Hence, the term "aperture" as used herein is not limiting.

An aliquot of sample 32 when passed through aperture 34 will cause a series of first pulses to be developed. The series of first pulses forming a first pulse train and consisting of $N_1$ pulses developed during one counting cycle, are coupled from aperture 34 to threshold circuit 42 and to summing circuit 43. Threshold circuit 42 is of a commonly known type such that when the input signal exceeds a predetermined level, a fixed amplitude output signal will be developed. For convenience, the pulses developed by threshold circuit 42 will be identified as first pulses. The pulses are passed to a counter 46 which counts each pulse and accumulates a total count.

Another similar aliquot of sample 32 when passed through aperture 36 will cause a series of second pulses to be developed in response to passage of the particles in this aliquot 32 through aperture 36. The series of second pulses forming a second pulse train and consisting of $N_2$ pulses are coupled from aperture 36 to summing circuit 43. The series of first pulses forming a first pulse train consisting of $N_1$ pulses coupled from aperture 34 and the series of second pulses forming a second pulse train consisting of $N_2$ pulses, are summed by summing circuit 43 to form a "fictitously doubled" train of pulses. Most pulses of train $N_1$ will fall between pulses of $N_2$, so that the "fictitiously doubled" train will contain slightly fewer than twice as many pulses as in either $N_1$ or $N_2$. A few pulses from $N_1$ and $N_2$ will occur simultaneously, creating a coincidence loss of the same nature as occurs in each individual aperture. The "fictitiously doubled" pulse train thus represents quite accurately the pulse train which would be produced by either aperture 34 or 36 if the concentration of particles in the sample were actually doubled exactly.

The "fictitiously doubled" train of pulses is passed from summing circuit 43 to threshold circuit 44. Threshold circuit 44 is identical to threshold circuit 42 and will develop a fixed amplitude output signal in response to each pulse coupled thereto which exceeds a predetermined level. The threshold signals are coupled from threshold circuit 44 to counter 48 where they are accumulated in order to provide a count of the "fictitiously doubled" pulse train. This "fictitiously doubled" count, $N_{FD}$, (FD standing for fictitiously doubled) for purposes of this application corresponds to the count of pulses developed by threshold circuit 44 in FIG. 4 of the parent patent application Ser. No. 443,428. Accordingly, the count $N_{FD}$ developed in counter 48 is the counterpart of the count represented by $N_2$ in the above equation (6). Consequently, equation (6), for purposes of a more clear understanding of the circuitry shown in FIG. 1 of the present application may be rewritten as follows:

$$N_0 = 2N_1 - (N_{FD}/2) \qquad (7)$$

The counts $N_1$ and $N_{FD}$ accumulated in counters 46 and 48 are fed to a calculator 50, which may, for example, be a computer in one embodiment and in another embodiment may be simple electronic circuitry. Calculator 50 will perform the multiplication and divisioon of the counts representing $N_1$ and $N_{FD}$ in accordance with equation (7) and yield a corrected count $N_0$. This corrected count may be displayed by a display device 52 which provides a visual display of the error corrected count $N_0$.

Because the structure shown in FIG. 1 is equivalent to the structure shown in FIG. 4 of the parent patent application Ser. No. 443,428 the same formulas for determining $N_0$, the true count, apply to both circuit implementations.

A method of further reducing the resultant statistical error over the statistical error occuring from use of the above apparatuses is to increase the number of particles counted by scanning an increased number of aliquots of sample, then substituting into equation (1) the count for each aliquot scanned and solving the resultant equations simultaneously for $N_0$ in terms of the counts taken.

Figure 2:
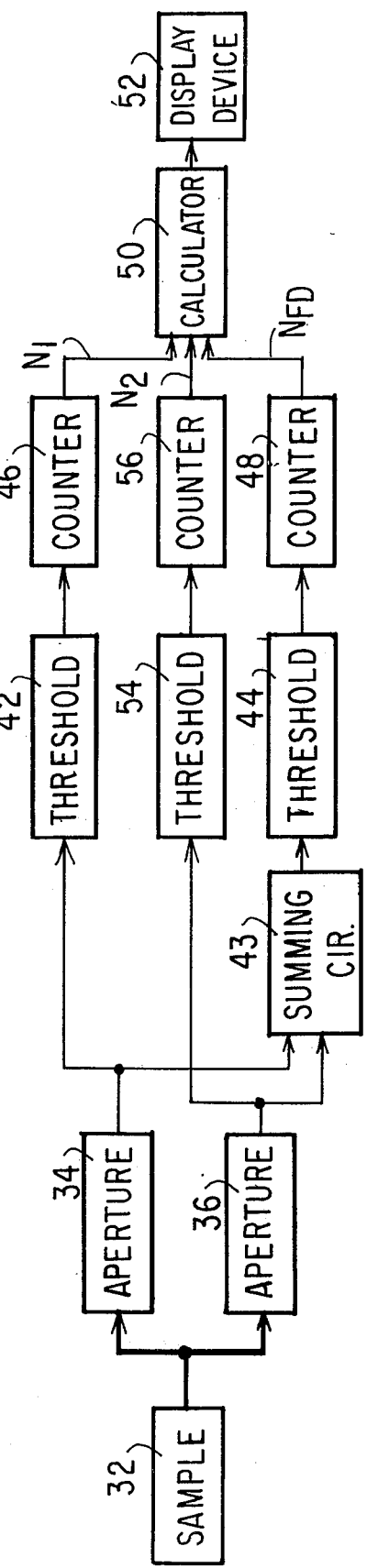
FIG. 2 is a block diagram of a particle analyzer employing coincidence error correction circuitry in accordance with one embodiment of the invention.

For the first embodiment of the invention, consider the sensing zones or apertures in the blocks 34 and 36 of FIG. 2 to each have the same dimensions, the same critical volume and scanning constant. The same size aliquot of sample 32 is introduced to apertures 34 and 36; being parts of the same sample, each has the same concentration. Sample 32 causes a series of first pulses forming a first pulse train consisting of $N_1$ pulses to be developed in response to passage of the particles in sample 32 through aperture 34. Sample 32 causes a series of second pulses forming a second pulse train consisting of $N_2$ pulses to be developed. The first pulse train $N_1$ and second pulse train $N_2$ are both coupled to summing circuit 43 where they are combined to produce a series of pulses forming a summed pulse train and represented by $N_{FD}$. From apertures 34 and 36 we have created three separate raw counts $N_1$, $N_2$ and $N_{FD}$. Substituting each into equation (1) we have:

$$N_1 = N_0 - KN_0^2 \qquad (8)$$

$$N_2 = N_0 - KN_0^2 \qquad (9)$$

$$N_{FD} = 2N_0 - 4KN_0^2 \qquad (10)$$

Simultaneous solution of equations (8), (9) and (10) yields:

$$N_0 = N_1 + N_2 - (N_{FD}/2) \qquad (11)$$

Referring again to FIG. 2, the above noted equation (11) is implemented therein with the first pulse train $N_1$ being coupled to threshold circuit 42 as in FIG. 1 and the artificially doubled pulse train $N_{FD}$ being coupled to threshold circuit 44 as in FIG. 1. The second pulse train $N_2$ is coupled to a threshold circuit 54, threshold circuit 54 being identical to threshold circuits 42 and 44. Accordingly, each pulse in the second pulse train which exceeds a predetermined level will cause threshold circuit 54 to develop an output signal which is passed to the counter 56. Counter 56 counts and accumulates each received threshold signal in order to develop a total raw count $N_2$. Counters 46 and 48 accumulate the threshold pulses from their respective threshold circuits 42 and 44 in order to develop raw counts $N_1$ and $N_{FD}$. The counts accumulated in each of counters 46, 48 and 56 are introduced to calculator 50 where they are mathematically manipulated in accordance with formula (11) in order to develop the true or corrected count $N_0$. In this particular version, calculator 50 adds the raw count $N_1$ and the raw count $N_2$, then operates to subtract from the sum of $N_1 + N_2$ half the fictitiously doubled count $N_{FD}/2$. The true or correct count $N_0$ is displayed by display device 52 as in FIG. 1 in order to provide a visual representation of the true or corrected count.

Referring to FIG. 3, there is shown an electronic implementation for the circuit configuration shown in FIG. 2. Those portions of FIG. 3 which are the same as FIG. 2 will not again be described. Only those portions containing changes from that shown in FIG. 2 will be discussed.

Counters 46, 48 and 56 and calculator 50 of FIG. 2 have been replaced in FIG. 3 with specific electrical circuitry. In FIG. 3 the threshold pulses developed by threshold circuit 42 are fed to a leading edge detector 60. Leading edge detector 60 responds to the leading edge of each threshold signal to develop a pulse which is coupled to a monostable multivibrator, or one shot 62. One shot 62 develops a fixed amplitude pulse having a fixed but very short duration in response to each pulse from leading edge detector 60 which is passed to one input of OR gate 64.

The threshold pulses developed by threshold circuit 54 in response to the second pulses in second pulse train $N_2$ also are fed to a leading edge detector 66 which is the same as leading edge detector 60. Each threshold signal fed to leading edge detector 66 will produce a pulse that is coupled from leading edge detector 66 to one shot 68. One shot 68 is identical to one shot 62 and will develop a pulse of fixed amplitude and very short but fixed duration in response to each pulse from leading edge detector 66. The pulses developed by one shot 68 are passed to a second input of OR gate 64. OR gate 64 will develop an output pulse in response to each pulse from either one shot 62 or 68. OR gate 64 then acts to add together the pulses in excess of the predetermined threshold level in the first and second pulse trains $N_1$ and $N_2$. By minimizing the period of the pulses developed by one shots 62 and 68 the possibility of an overlap due to the presence of pulses from both, is substantially reduced thus reducing the possibility of an error in counting or adding together the numbers of pulses in pulse trains $N_1$ and $N_2$.

The pulses or logical "one" state signals developed at the output of OR gate 64 and representing the added together pulse train counts $N_1$ and $N_2$ are fed to the up input of an up-down counter 70. Each one state signal coupled from OR gate 64 will cause up-down counter 70 to add one to the total accumulated count.

Threshold pulses developed by threshold circuit 44 are coupled to a divider circuit 80. Divider circuit 80 is of the type now well known in the art which will develop one pulse at its output in response to every two pulses at its input. This can take the form of a standard bistable commonly known as a flip-flop. In effect then, divider circuit 80 divides the number of pulses received by two and develops half as many pulses at its output as are present in its input. Accordingly, a series of pulses will be developed at the output of divider circuit 80 equivalent to $N_{FD}/2$ as shown in equatioon (11). The number of pulses in the pulse train $N_{FD}$ has therefore been mathematically manipulated, that is divided, as is required by equation (11).

The pulses developed by divider circuit 80 are fed to a leading edge detector 82. Leading edge detector 82 is identical to leading edge detectors 60 and 66 and develops a pulse in response to the leading edge of each pulse fed from divider circuit 80. The pulses developed by leading edge detector 82 are coupled to a one shot 84 which is identical to one shots 62 and 68. One shot 84 develops a fixed amplitude and fixed but very short duration pulse in response to each pulse from leading edge detector 82. The pulses developed by one shot 84 are fed to the down input of up-down counter 70. Each pulse fed from one shot 84 to the down input of up-down counter 70 will cause up-down counter 70 to remove or subtract one from the total count accumulated therein.

Up-down counter 70 will continue to count up and down in response to each pulse coupled thereto until the entire sample has been passed through each of apertures 34 and 36 and every pulse in excess of the threshold level of thresholds 42, 44 and 54 has been counted. When every pulse has been counted, the number accumulated in up-down counter 70 will be $N_0$, the true or corrected count. This count will be displayed by display device 52 to allow a visual presentation of the corrected count $N_0$.

As noted previously, the corrected count $N_0$ is statistically more accurate using the apparatus shown in FIGS. 2 and 3 as compared to the apparatus shown in FIG. 1 because an additional raw count has been taken. The premises or theory resulting in the apparatus shown in FIGS. 2 and 3 and equations (8) through (11) can be extended to any number of apertures. For example, three apertures may be employed rather than two with each aperture having substantially the same dimensions, substantially the same critical volume and scanning constant.

Referring now to FIG. 4 in this embodiment of the invention, three apertures 34, 36 and 90 are provided, with all three meeting the criteria previously noted. An aliquot of sample 32 when introduced to aperture 34 will cause a series of first pulses to be developed in response to passage of the particles in sample 32 through aperture 34 with the series of first pulses forming a first pulse train consisting of $N_1$ pulses. The same size aliquot of sample 32 when introduced to aperture 36 will cause a series of second pulses to be developed in response to passage of the particles in sample 32 through aperture 34 with the series of second pulses forming a second pulse train consisting of $N_2$ pulses. An aliquot of sample 32 when introduced to aperture 90 will cause a series of third pulses to be developed in response to the passage of particles in sample 32 through aperture 90 with the series of third pulses forming a third pulse train consisting of $N_3$ pulses. The pulses forming each of the pulse trains $N_1$, $N_2$ and $N_3$ are coupled from apertures 34, 36 and 90 to summing circuit 43 where they are summed to form a fictitiously tripled pulse train having a number of pulses represented by $N_{FT}$ (FT representing fictitiously tripled). Substituting the raw counts $N_1$, $N_2$, $N_3$ and $N_{FT}$ into equation (1) we obtain:

$$N_1 = N_0 - KN_0^2 \quad (12)$$
$$N_2 = N_0 - KN_0^2 \quad (13)$$
$$N_3 = N_0 - KN_0^2 \quad (14)$$
$$N_{FT} = 3N_0 - K(3N_0)^2 \quad (15)$$

Solving all four equations simultaneously we obtain:

$$N_0 = \frac{N_1 + N_2 + N_3}{2} - \frac{N_{FT}}{6} = \frac{N_1}{2} + \frac{N_2}{2} + \frac{N_3}{2} - \frac{N_{FT}}{6} \quad (16)$$

Referring again to FIG. 4, the circuit implementation for equation (16) is shown. As can be seen, portions are substantially the same as certain portions of the circuit implementation shown in FIG. 3. Those portions which are the same will be given the same reference number. The path which develops the raw count $N_1/2$ includes aperture 34, threshold circuit 42, divider circuit 92, leading edge detector 60 and one shot 62. This path operates in the same manner as the path for developing the raw count $N_1$ in FIG. 3 with the exception of the additional divider 92. Divider 92 divides the number of threshold pulses by two so that the output of one shot 62 in FIG. 4 is a series of pulses representing the quantity $N_1/2$.

The path for developing the quantity $N_2/2$ includes aperture 36, threshold circuit 54, divider circuit 94, leading edge detector 66 and one shot 68. This path functions in substantially the same manner as the corresponding path in FIG. 3 with the exception of the additional divider 94. Divider 94 divides the number of threshold pulses by two so that the output of one show 68 is a series of pulses representing the quantity $N_2/2$.

A new path is included in the apparatus shown in FIG. 4 consisting of aperture 90, threshold circuit 96, divider circuit 98, leading edge detector 100 and one shot 102. The components and operation are identical to that described with reference to the two preceding paths and function to produce a series of pulses at the output of one shot 102 which represents the quantity $N_3/2$.

The output of one shots 62, 68 and 102 are fed to the inputs of OR gate 64 which acts to add the pulses from each path so that the output from OR gate 64 represents the addition of $(N_1 + N_2 + N_3)/2$. The pulses developed by OR gate 64 are passed to the up input of up-down counter 70 in the same manner as shown and described with respect to FIG. 3, in order to accumulate a total count representative of $(N_1 + N_2 + N_3)/2)$.

The path consisting of summing circuit 43, threshold circuit 44, divider circuit 104, leading edge detector 82 and one shot 184 operates in a manner identical to that shown for the corresponding path in FIG. 3, with the exception that divider 104 divides by 6 in FIG. 4 as compared to division by two in FIG. 3. Accordingly, for every six pulses fed to the input of divider 104, it will develop one pulse at its output so that the pulses developed at the output of one shot 84 represent the raw count $N_{FT}/6$. These pulses are passed from the output of one shot 84 to the down input of up-down counter 70. Each pulse received causes one to be substracted from the total count accumulated in up-down counter 70.

When each aliquot of the sample 32 has passed through the apertures 34, 36 and 90 and all pulses have been counted, the number accumulated in up-down counter 70 will represent the corrected count $N_0$ as shown in equation (16). This corrected count number is displayed by display device 52 in order to provide a visual representation of the true or correct count.

As can be seen, the theory or premise recognized and employed herein may be extended to any number of apertures with each additional aperture producing an increase in statistical accuracy. Furthermore, although one specific equation for $N_0$ has been employed in order to solve equations simultaneously and derive the resultant formulas and circuits, it is to be understood that other specific formulas for $N_0$, which are equally valid, may be employed in the same manner for developing other circuit configurations employing a plurality of apertures and resulting in a greater statistical accuracy. Accordingly, the specific examples given are not to be considered as limiting the appended claims.

What is sought to be protected by United States Letters Patent is:

1. In a particle analyzer subject to coincidence errors in counting particle pulses the combination including:
   at least first and second sensing means each having substantially the same dimensions and each generating a train of particle pulses in response to passage through each of said sensing means of a sample containing a plurality of particles to be counted,
   summing circuit means coupled to each of said sensing means for summing together each of said generated trains of particle pulses to develop a summed train of pulses, and
   circuit means coupled to said summing means and to each of said sensing means for receiving separately said each generated train of particle pulses and said summed train of particle pulses, said circuit means being operative to mathematically change at least the number of particle pulses in said summed train of pulses in accordance with a particular mathematical formula, and to accumulate said numbers of pulses in said generated trains of pulses received and said mathematically changed summed train of pulses to produce an error corrected particle pulse count.

2. The particle analyzer of claim 1 wherein said circuit means include; counter means coupled to said summing circuit means and to each of said sensing means to accumulate said numbers of pulses, said counter means counting in a first counting direction in response to certain ones of said pulse trains and in the other counting direction in response to other ones of said pulse trains.

3. The particle analyzer of claim 2 wherein said counter means is an up-down counter.

4. The particle analyzer of claim 3 wherein said up-down counter counts up in response to each pulse in said generated train of particle pulses from said first and second sensing means and down in response to each pulse in said mathematically changed summed train of pulses.

5. The particle analyzer of claim 4 wherein said circuit means include divider means coupled between said summing circuit means and said up-down counter and operative in response to said summed train of pulses to develop said mathematically changed number of pulses having one-half the number of pulses as said summed train of pulses.

6. The particle analyzer of claim 2 wherein said circuit means further include a plurality of detector means, each coupling one of said summing circuit means and said sensing means to said counter means, said detector means each being operative in response to pulses in excess of a predetermined amplitude to develop pulses to be counted.

7. The particle analyzer of claim 6 wherein said detector means coupled between said sensing means and said counter means further include divider means operative in response to said summed train of detected pulses to develop said mathematically changed number of pulses having one-half the number of pulses as the detected summed train of pulses.

8. The particle analyzer of claim 1 wherein said first sensing means generates a train of pulses having a first particular number $N_1$, said second sensing means generates a train of pulses having a second particular number of $N_2$, and said summing means develops a summed train of pulses having a particular number $N_{FD}$, said circuit means being operative to accumulate said number of pulses in said trains of pulses in accordance with the formula $$N_0 = N_1 + N_2 - (N_{FD}/2)$$

where $N_0$ is the error corrected count.

9. The particle analyzer of claim 1 including a third sensing means having substantially the same dimensions as said first and second sensing means and generating a train of particle pulses in response to passage therethrough of a sample containing a plurality of particles to be counted, said summing means being coupled to the said third sensing means for summing said train of particle pulses generated by said third sensing means with said train of pulses developed by said first and second sensing means.

10. The particle analyzer of claim 9 wherein said first sensing means generates a train of pulses having a first particular number $N_1$, said second sensing means generates a train of pulses having a second particular number $N_2$, said third sensing means generates a train of pulses having a third particular number $N_3$, and said summing means develops a summed train of pulses having a particular number $N_{FD}$, said circuit means being operative to accumulate said numbers of pulses in said trains of pulses in accordance with the formula $$N_0 = \frac{N_1}{2} + \frac{N_2}{2} + \frac{N_3}{2} + \frac{N_{FD}}{6}$$

where $N_0$ is the error corrected count.

11. The particle analyzer of claim 9 wherein said circuit means include counter means coupled to said summing circuit means and to each of said sensing means to accumulate said numbers of pulses, said counter means counting in a first counting direction in response to certain ones of said pulse trains and the other counting direction in response to other ones of said pulse trains.

12. The particle analyzer of claim 11 wherein said counter means is an up-down counter.

13. The particle analyzer of claim 11 wherein said circuit means include three detector means each coupling one of said summing circuit means and said sensing means to said counter means, said detector means each being operative in response to pulses in excess of a predetermined amplitude to develop pulses to be counted.

14. The particle analyzer of claim 13 wherein said detector means coupling said summing circuit means to said counter means include first divider means operative in response to said trains of pulses coupled thereto to develop trains of pulses having one-half the number of pulses as coupled thereto, and second divider means operative in response to said summed train of detected pulses to develop said mathematically changed number of pulses having one-sixth the number of pulses as said detected summed train of pulses.

15. The particle analyzer of claim 14 wherein said up-down counter counts up in response to each pulse from said first divider means and down in response to each pulse from said second divider means.

16. In a particle analyzer subject to coincidence errors in counting particle pulses the combination including:

a first sensing means for generating a first train of particle pulses having a first number of particle pulses in response to passage through said first sensing means of a sample containing a plurality of particles to be counted, a second sensing means having substantially the same dimensions as said first sensing means for generatiang a second train of particle pulses having a second number of particle pulses in response to passage through said second sensing means of a sample containing a plurality of particles to be counted, summing circuit means coupled to said first and second sensing means for summing together said first and second trains of particle pulses to develop a third train of particle pulses having a third number of particle pulses, first, second and third pulse detection means coupled to said first and second sensing means and said summing circuit means respectively and operative in response to pulses in excess as a predetermined amplitude to develop first, second and third trains having first, second and third numbers of detected pulses, divider means coupled to said third detection means and operative in response to said third detected pulses to develop a train of pulses having one-half the number of said third detected pulses, and up-down counter means coupled to said first and second detection means and said divider means and operative in response to said pulses in said first and second trains of detected pulses to count up and operative in response to said pulses from said divider means to count down, said counter means developing a total count therein which is an error corrected particle pulse count.

* * * * *